United States Patent [19]

Chitwood

[11] Patent Number: 5,569,175
[45] Date of Patent: Oct. 29, 1996

[54] PIVOTABLE CERVICAL TRACTION/STRETCH AND NECK CURVE SUPPORT DEVICE

[75] Inventor: Ralph Chitwood, Whitefish, Mont.

[73] Assignee: Glacier Cross, Inc., Kalispell, Mont.

[21] Appl. No.: 327,021

[22] Filed: Oct. 21, 1994

Related U.S. Application Data

[63] Continuation-in-part of Ser. No. 120,602, Sep. 13, 1993, Pat. No. 5,441,479.

[51] Int. Cl.$^6$ ............................................. A61H 1/00
[52] U.S. Cl. ........................ 602/32; 602/13; 602/36; 601/39; 128/845; 128/DIG. 20
[58] Field of Search ............................. 128/845, 870, 128/DIG. 20; 601/15, 24, 39, 148–152; 602/13, 32, 33, 35, 36; 5/622, 636, 637, 640, 644

[56] References Cited

U.S. PATENT DOCUMENTS

| D. 344,135 | 2/1994 | Price. | |
|---|---|---|---|
| 2,638,091 | 5/1953 | Varco. | |
| 2,817,524 | 12/1957 | Sadler | 482/117 |
| 3,570,479 | 3/1971 | Horn. | |
| 4,103,681 | 8/1978 | Shanley. | |
| 4,123,104 | 10/1978 | Andres et al. | 297/391 |
| 4,166,459 | 9/1979 | Nightingale | 602/32 |
| 4,204,529 | 5/1980 | Cochrane. | |
| 4,473,912 | 10/1984 | Scheidel et al.. | |
| 4,508,109 | 4/1985 | Saunders. | |
| 4,583,255 | 4/1986 | Mogaki et al. | 601/150 |
| 4,627,422 | 12/1986 | Bates. | |
| 4,700,696 | 10/1987 | Schoffstall. | |
| 4,702,235 | 10/1987 | Hong | 602/13 |
| 4,736,736 | 4/1988 | Moers et al.. | |
| 4,805,603 | 2/1989 | Cumberland | 602/13 |
| 4,826,152 | 5/1989 | Lo | 482/114 |
| 4,934,354 | 6/1990 | Anapliotis | 602/32 |
| 5,020,520 | 6/1991 | Lawlis. | |
| 5,067,483 | 11/1991 | Freed. | |
| 5,074,287 | 12/1991 | Avitt. | |
| 5,100,131 | 3/1992 | Fong. | |
| 5,181,904 | 1/1993 | Cook et al. | 602/32 |
| 5,201,702 | 4/1993 | Mars. | |
| 5,336,138 | 8/1994 | Arjawat | 482/10 |
| 5,382,226 | 1/1995 | Graham. | |

FOREIGN PATENT DOCUMENTS 760971   9/1980   U.S.S.R. ............................. 602/32

Primary Examiner—Linda C. Dvorak
Assistant Examiner—Jeanne M. Clark
Attorney, Agent, or Firm—Thomas R. Vigil

[57] ABSTRACT

The pivotable cervical traction/stretch and neck curve support device comprises a base portion having an upper inclined surface for supporting a person's upper body or torso, a table or platform situated adjacent the base portion and having an upper surface and a bottom surface, a pivotable mounting mechanism attached to the base for pivotally and rotatably mounting the platform to the base in a manner allowing rotation of the platform about any one of or all of an X-axis, a Y-axis and a Z-axis. The mounting mechanism includes structure for securing the platform in a desired position, a head portion having an inner surface and a bottom surface, the bottom surface being in sliding contact with the platform, the head portion also having specially contoured surfaces for receiving a person's head, and a mechanism for incrementally moving the head portion on the platform away from the inclined surface.

17 Claims, 5 Drawing Sheets

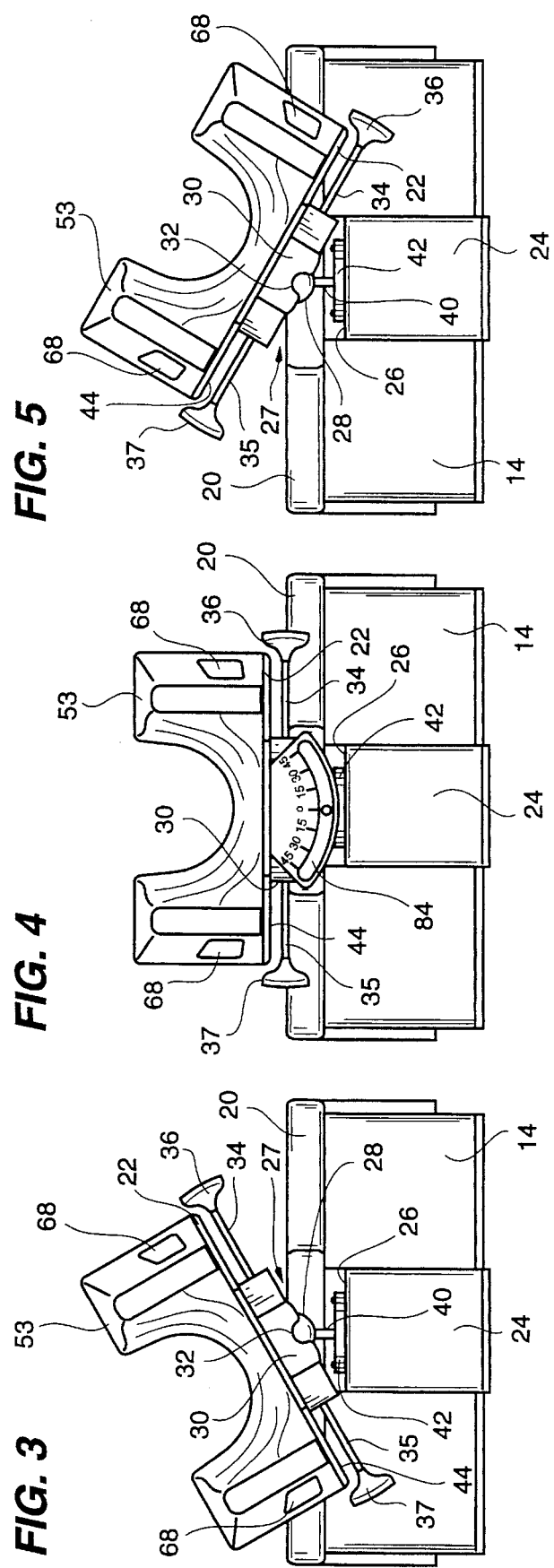

PIVOTABLE CERVICAL TRACTION/STRETCH AND NECK CURVE SUPPORT DEVICE

This application is a continuation-in-part of U.S. patent application Ser. No. 08/120,602 filed on Sep. 13, 1993, now U.S. Pat. No. 5,441,479, issued on Aug. 15, 1995.

BACKGROUND OF THE INVENTION

1. Field of the Invention

The present invention relates to a pivotable cervical traction/stretch and neck curve support device which includes a base having an inclined surface for supporting a person's upper body or torso, a platform positioned above the base, structure attached to the base (a) for rotatably mounting the platform to the base, (b) for allowing rotation of the platform about any or all of an X-axis, a Y-axis and a Z-axis and (c) for securing the platform in a desired position. The traction/stretch and neck curve support device further includes a head portion on the platform and a mechanism for moving the head portion upwardly in an inclined direction against the occipital bone of a patient's head received in the head portion.

2. Description of the related art including information disclosed under 37 CFR §§1.97–1.99.

Heretofore it has been proposed in the Cumberland U.S. Pat. No. 4,805,603 to provide a cervical traction/stretch and neck curve support device comprising a head/neck/shoulder support unit having a vertical slot in the region corresponding to the cervical area. The slot separates the unit into a first section and a second section. The upper surfaces of each of the sections is shaped to receive the head, neck and shoulders of a reclining person. An inflatable air sack is located within the unit between the first and second sections and a hand operated bulb type air pump is provided for pumping up the air sack.

Also in applicant's earlier application, serial number 08/120,602, the disclosure of which is incorporated herein there is disclosed a cervical traction/stretch and neck curve support device comprising a body including a shoulder portion, a head portion and a bellows which extends substantially across the width and height of the body between and connected to the head portion and to the shoulder portion and acting against and between substantially the full inner end surface of the head portion and the full inner end surface of the shoulder portion. The bellows, the shoulder portion and the head portion having aligned U-shaped openings therein adapted to receive a patients neck. A hand operated air pump is provided for pumping air into the bellows and for releasing air from the bellows. The head portion has a head receiving surface including a shoulder with an adjacent occipital cervical pressure or lift surface for engaging a user's head.

The traction/stretch created by the traction/stretch and neck curve support device of the present invention is designed to create an even separation of the anterior and posterior vertebrae versus a jamming in the anterior to create an opening in the posterior of the vertebral column as incurred with prior art traction devices.

SUMMARY OF THE INVENTION

According to the present invention there is provided a pivotable cervical traction/stretch and neck curve support device comprising: a base portion having an upper end, an upper inclined surface extending upwardly to the upper end for supporting a person's upper body or torso and a lower surface for resting on a planar support surface; a table or platform situated adjacent the upper end of the base portion and having an upper surface and a bottom surface; mounting structure attached to the upper end of the base and to the bottom surface of the platform for pivotally and rotatably mounting the platform to the upper end of the base and above the upper end of the base in a manner allowing rotation of the platform about any one of or all of an X-axis, a Y-axis and a Z-axis, the mounting structure including a mechanism for securing the platform in a desired position; a head portion having an inner end surface, a bottom surface and a head receiving surface including a shoulder with an adjacent occipital cervical pressure or lift surface for engaging a user's head, the bottom surface being slidably supported on the platform; and a mechanism positioned on the platform, including a bellows portion and operable by the user or a healthcare practitioner for incrementally moving the head portion on the platform outwardly from the inclined surface.

BRIEF DESCRIPTION OF THE DRAWINGS

FIG. 3 is a rear view of the cervical traction/stretch and neck curve support device shown in FIG. 1 and shows the platform tilted 30° to the right from the starting position.

FIG. 4 is a rear view of the cervical traction/stretch and neck curve support device shown in FIG. 1 and shows the platform in the first or starting position.

FIG. 5 is a rear view of the cervical traction/stretch and neck curve support device shown in FIG. 1 and shows the platform tilted 30 degrees to the left from the starting position.

DESCRIPTION OF THE PREFERRED EMBODIMENT

Figure 1:
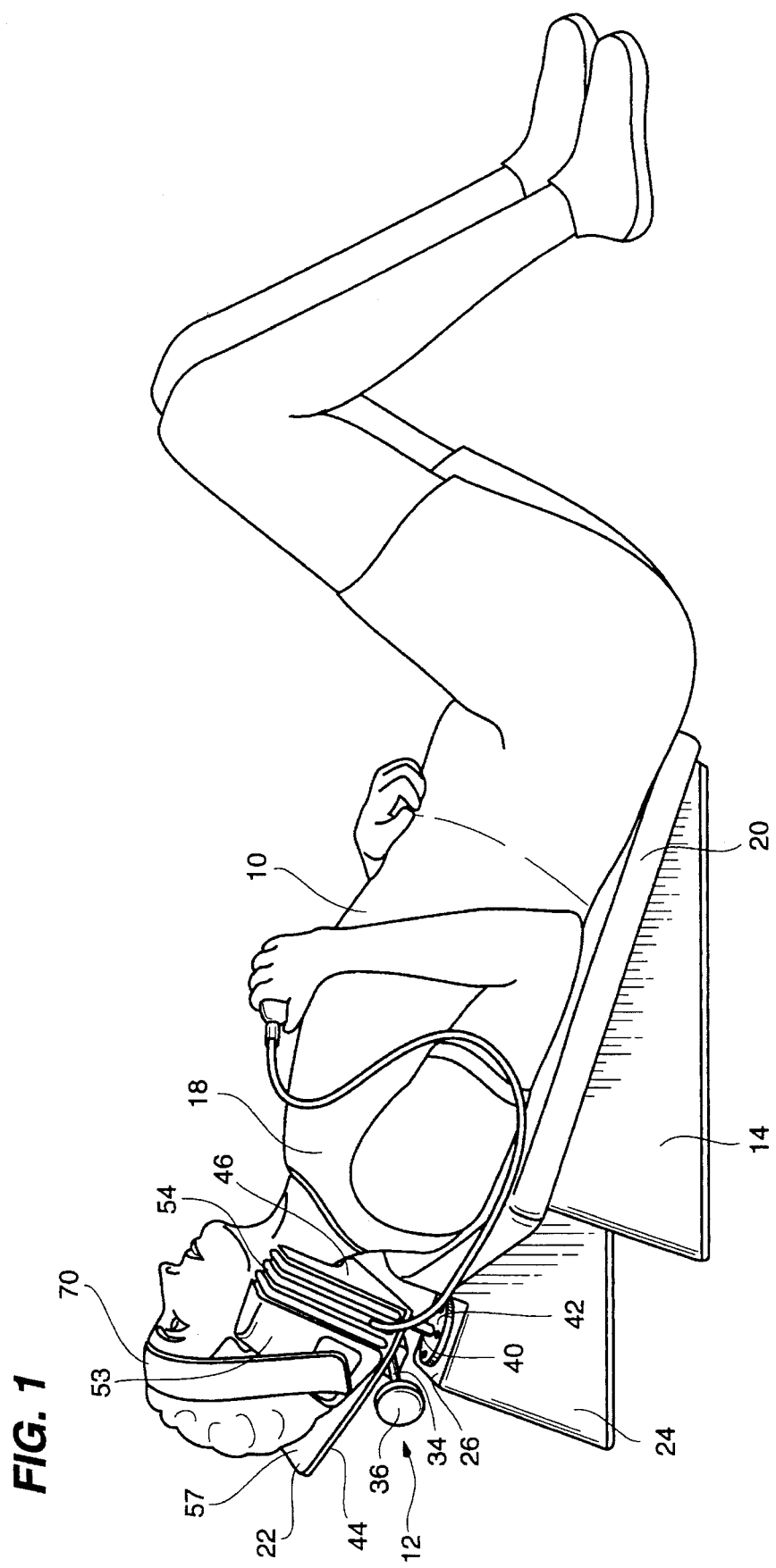
FIG. 1 is a perspective view of the pivotable cervical traction/stretch and neck curve support device constructed according to the teachings of the present invention.

Referring now to the drawings in greater detail there is illustrated in FIG. 1 a person 10 positioned on a pivotable cervical traction/stretch and neck curve support device 12 constructed according to the teachings of the present invention. The device 12 includes a base portion 14 having an inclined surface 16 (FIG. 2) for supporting the person's upper body or torso 18.

A foam pad 20 is shown placed on the inclined surface 16 (FIG. 2) to provide comfort to the person using the device 12 as well as to encourage the person's upper body or torso 18 to slip down the inclined surface 16 (FIG. 2) allowing the benefit of gravity traction in lower (thoracic) vertebrae.

Figure 2:
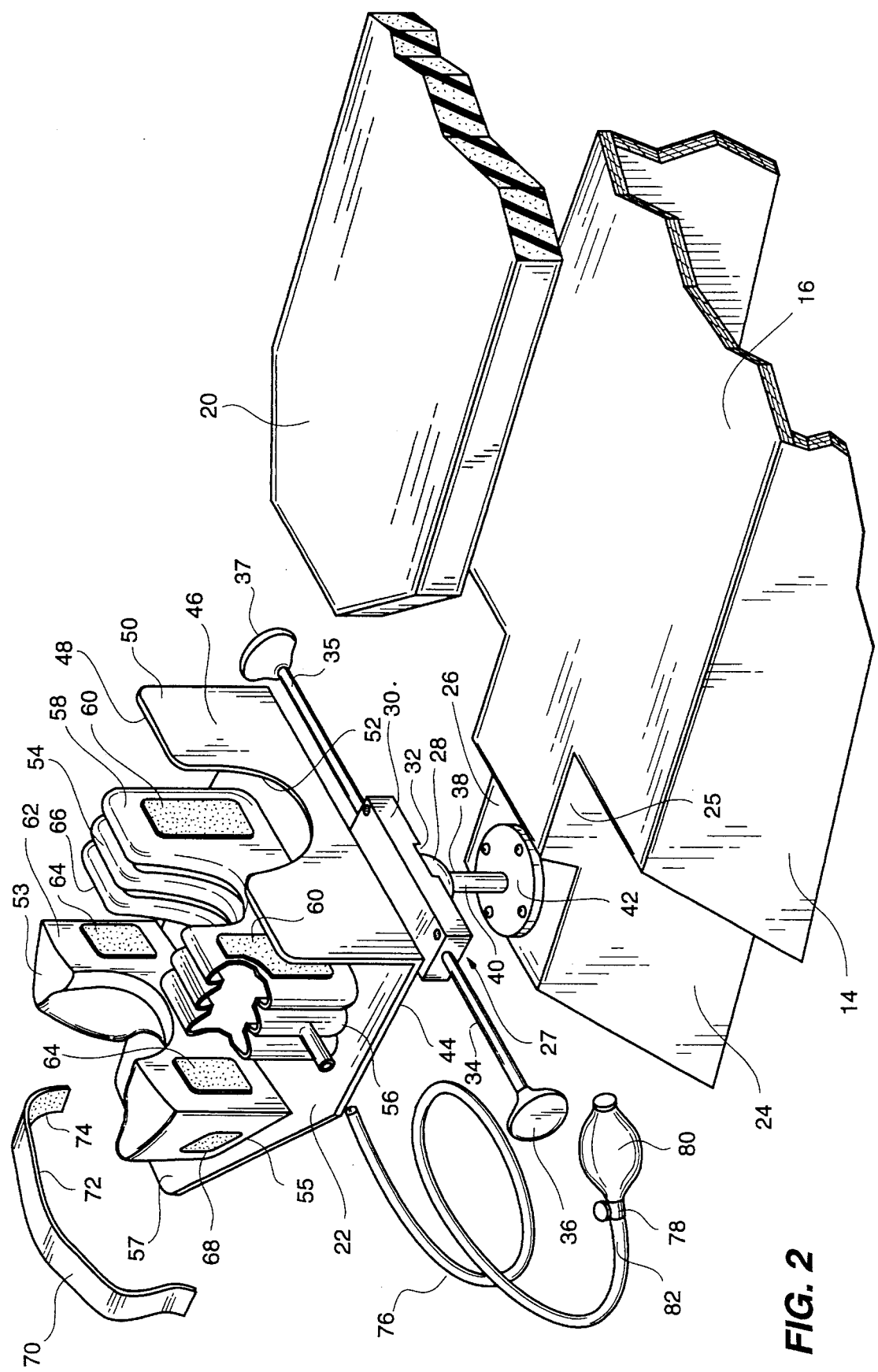
FIG. 2 is an exploded perspective view of the cervical traction/stretch and neck curve support device shown in FIG. 1 with portions cut away.

As can be see in FIG. 2, the device 12 further includes a pivotable table or platform 22 which is pivotally mounted to a pedestal portion 24 of the base portion 14. The pedestal portion 24 is located below an upper end 25 of the inclined surface 16 (FIG. 2).

As shown in FIG. 2, pedestal portion 24 is stepped down from the inclined surface 16 of the base portion 14 and has a flat surface 26 which extends parallel to inclined surface 16.

Figure 9:
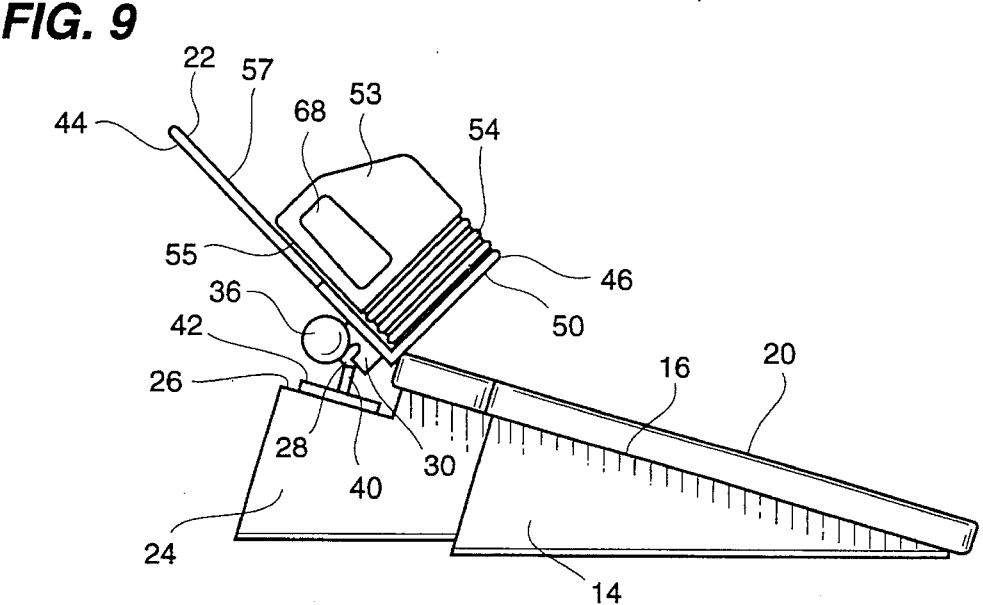
FIG. 9 is a side view of the cervical traction/stretch device shown in FIG. 1 and shows the platform tilted upwardly 30 degrees from a starting position.
Figure 10:
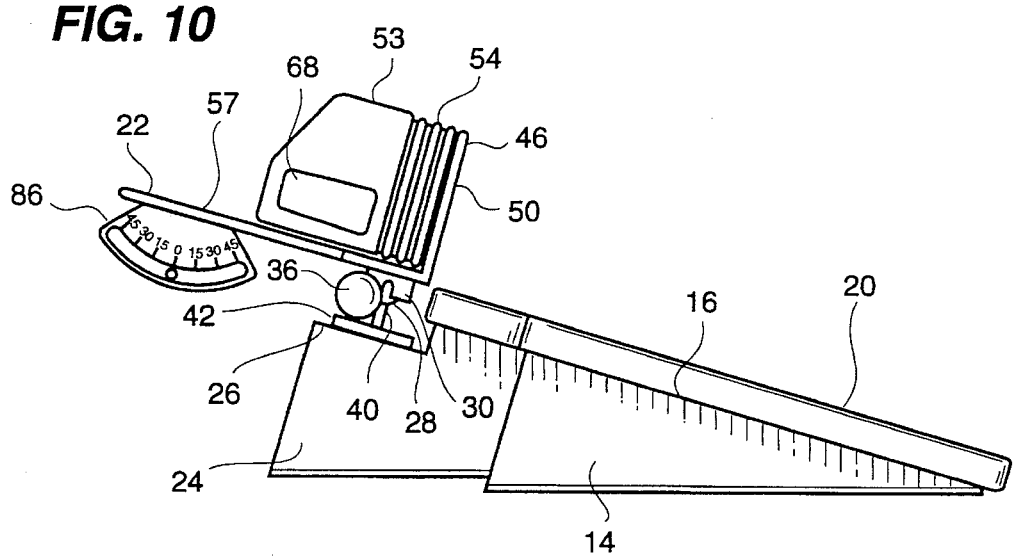
FIG. 10 is a side view of the cervical traction/stretch device shown in FIG. 1 and shows the platform in the first or starting position.
Figure 11:
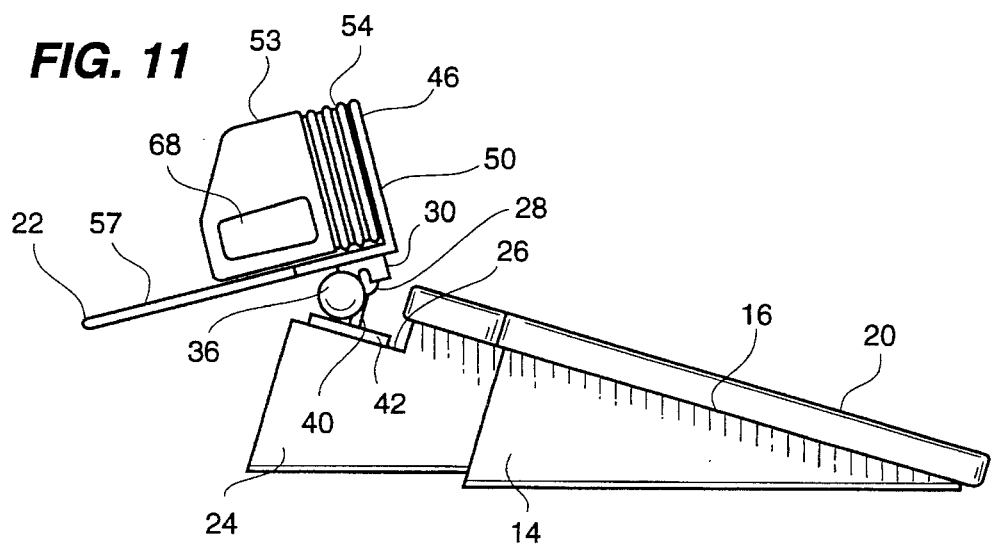
FIG. 11 is a side view of the cervical traction/stretch device shown in FIG. 1 and shows the platform tilted downwardly 30 degrees from the starting position.

As shown, the table or platform 22 is pivotally mounted to the pedestal portion 24 by a ball and socket assembly 27 (see FIGS. 9, 10 and 11). The ball and socket assembly 27 includes a ball 28, a bracket 30 having a socket 32 therein and two control rods 34, 35 threaded through the bracket 30 and having outer knobs 36 and 37. The ball 28 is mounted to an upper end 38 of a post 40 which is fixed to a circular base plate 42 which is mounted to the pedestal portion 24.

The bracket 30 is mounted to a bottom side 44 of the table or platform 22. The ball 28 is received in the socket 32 of the bracket 30 and can be rotated within the socket 32 about an X, a Y and a Z axis.

The control rods 34, 35 are threaded through the bracket 30 and when fully threaded into the bracket 30 engage the ball 28. When the control rods 34, 35 engage the ball 28, the platform 22 is locked in position and can not be rotated.

When the control rods 34, 35 are loosened, the platform 22 can be rotated about any one of (or all of) the X, Y and Z axis(es), as will be described below, in order to provide isolated traction for a person.

A plate 46 is mounted transversely to the table or platform 22. The plate 46 has an outer facing surface 48 and an inward facing surface 50. The plate 46 also has a U-shaped opening 52 therein.

The pivotable cervical traction/stretch and neck curve support device 12 also includes a head receiving portion 53 and a bellows portion 54 which are slidably mounted on a top surface 57 of the platform 22. A bottom surface 55 of the head portion 53 slidably contacts the top surface 57 of the platform 22 and, similarly, a bottom surface 56 of the bellows portion 54 slidably contacts the top surface 57 of the platform 22.

An inner side or surface 58 of the bellows portion 54 is secured, such as by an adhesive or by hook and loop type fastening structure 60 of the type sold under the trademark VELCRO®, to the outer facing surface 48 of the transverse plate 46.

Also as shown in FIG. 2, an inner facing surface 62 of the head portion 53 is secured, such as by an adhesive or by hook and loop type fastening structure 64 of the type sold under the trademark VELCRO®, to an outer facing surface 66 of the bellows portion 54.

Further details on the construction of the head receiving portion 53 and the bellows portion 54 are found in co-pending application Ser. No. 08/120,602 of which this application is a continuation-in-part and the disclosure of which is incorporated herein by reference.

Important features of the traction/stretch and neck curve support device 12 which are fully described in the parent application with reference numerals, are generally described below without reference numerals.

The head receiving portion 53 has a generally arcuate or semi-cylindrical U-shaped surface having a portion that inclines slightly downwardly at the center to fit and support the cervical curve of the patient's neck and has a head receiving surface having a center portion that curves downwardly for mating with the cervical curve.

The U-shaped surface extends toward the outer end of the head portion a distance approximately ¾ of an inch to one inch and forms a shoulder on opposite sides of the U-shaped curved surface but not at the center of the U-shaped curved surface. There is small shoulder on the U-shaped surface at the bottom of the U connecting with the surface portion of the head receiving surface.

Part way up either side of the U-shaped surface the shoulder is pronounced and is located at the junction between the U-shaped surface and the specially contoured head receiving surface. The shoulder at this location is adapted to bear against the occipital bone and defines in the head receiving surface an occipital-cervical pressure or lift surface just outwardly of the shoulder.

This shoulder and the adjacent pressure or lift surface on the head receiving surface enables the head receiving portion 53 to apply pressure at the region of the occipital bone of a patient on each side of the neck. It is believed that this pressure on the occipital bone applied with the cervical traction/stretch and neck curve support device also can alleviate or relieve headache pain.

Most cervical injuries to patients involve the loss of the natural cervical curve forming a so called military neck or straight neck syndrome. This creates stress on the upper thoracic muscles, as these muscles are forced to hold the head upright. When the natural curve is in place, the head weight is distributed throughout the skeletal system. The head portion 53 and bellows portion 54 of the pivotable cervical traction/stretch and neck curve support device 12 is constructed so that the patient's cervical curve is supported to relieve upper thoracic muscles from unnatural stress.

If desired, the device 12 can be constructed with a longer inclined surface 16 on the base portion 14 and the inclined surface 16 can be arranged to be pivoted through an arc of between 20 degrees and 70 degrees to the horizontal so that the force of gravity acting on the person 10 can be used to create the desired lift pressure on the occipital bone. In this modified embodiment, the bellows portion 54 may not be needed and can be left out.

Referring again to FIG. 2, the head portion 53 has on either side of the head portion 53, a loop and hook type fastening structure 68 of the type sold under the trademark VELCRO® and a head strap 70 which is adapted to be received over a patient's head and secured to the fastening structure 68.

The strap 70 has on its inner surface 72 a fabric attachment structure 74 of the type sold under the trademark VELCRO® on the inside of the strap 70 which, at each end of the strap 70, is adapted to be received over a patient's forehead and secured to the fastening structure 74. This is shown in FIG. 1 where a patient's head is shown resting in the head portion 53 of the pivotable cervical traction/stretch and neck curve support device 12 with the head strap 70 extending over the forehead and being connected to the fastening structures 68 on either side of the head portion 53. The head strap 70 holds the patient properly and securely for the best benefit of occipital lift and immobilizes the patient for accuracy in treatment.

A tubing 76 is connected to the bellows portion 54 and an release or relief valve 78 is connected to the tubing 76. A resilient bulb 80 is connected to the outer end 82 of the tubing 76 and has a one-way inlet valve 83 at the outer end of the bulb 80 to enable a patient to pump-up the bellows portion 54 to place a comfortable "lift" pressure on the occipital bone. Further details on the construction of the tubing 76 and the release valve 78 are found in application Ser. No. 08/120,602 the disclosure of which is incorporated herein by reference.

The pivotable cervical traction/stretch and neck curve support device 12 disclosed herein provides the ability to isolate an area for traction and concentrate treatment to the area of the stress by rotating the platform 22 slowly once a person's head is secured in the head portion 53 of the traction/stretch and neck curve support device 12 to find a position which places traction primarily on a desired area. After such a position has been determined, subsequent traction treatment of the area can be quickly and easily applied. Operation of the device 12 is explained below.

As shown in FIGS. 3, 4, and 5 the table or platform 22 can be rotated about an X-axis which is perpendicular to the drawing sheet. As shown in FIG. 3, the platform 22 is rotated about the X-axis approximately 30 degrees to the left of a first or starting position.

As shown in FIG. 4, the bottom side 44 of the platform 22 is parallel to the ground surface. A gauge 84 (shown in FIG. 4 only) can be provided for determining the amount of rotation of the platform 22 about the X-axis in the Y plane or the Z plane. A similar gauge can be provided for determining rotation about the Y or Z axis.

FIG. 5 shows the platform 22 rotated about the X-axis approximately 30 degrees to the right of the starting position shown in FIG. 4.

The platform 22 can be rotated up to 45 degrees in either the right or the left direction and can be stopped at any angle in between.

Figure 6:
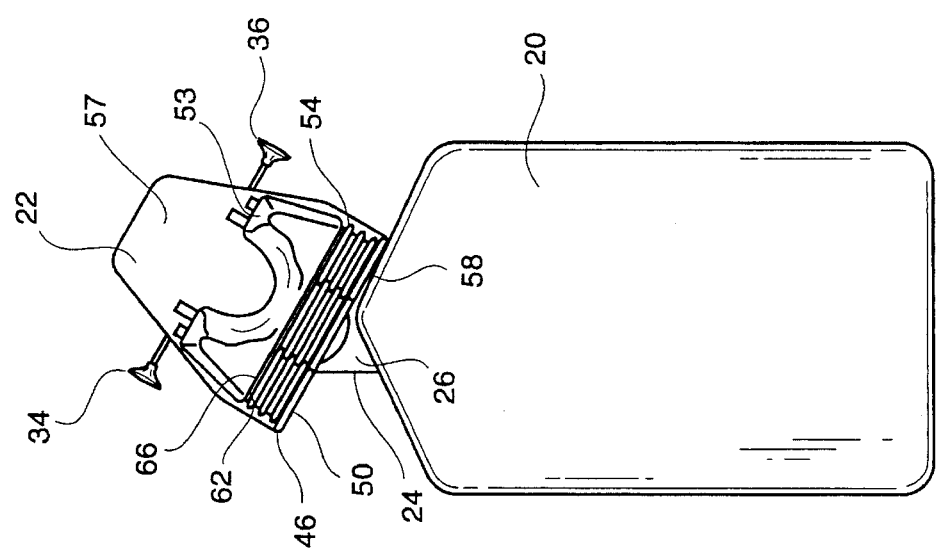
FIG. 6 is a top view of the cervical traction/stretch and neck curve support device shown in FIG. 1 and shows a platform of the device rotated 30 degrees to the left from a first position.
Figure 7:
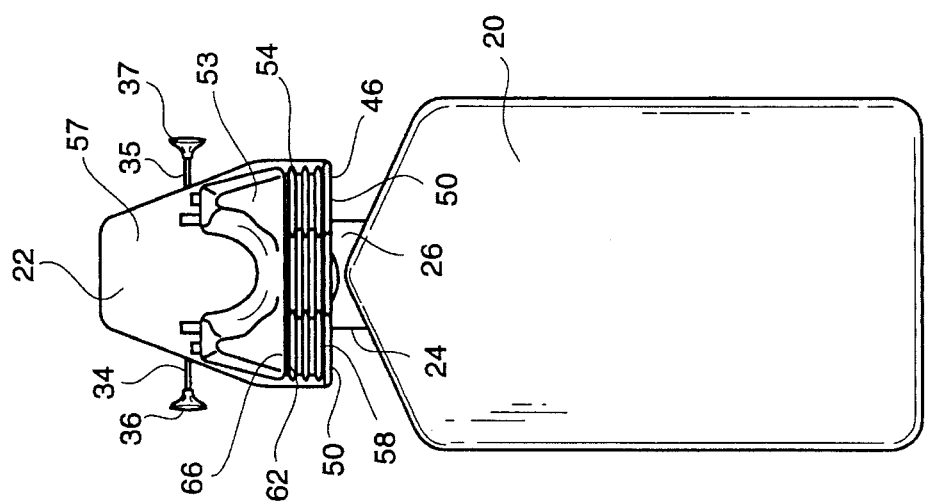
FIG. 7 is a top view of the cervical traction/stretch and neck curve support device shown in FIG. 1 and shows the platform of the device at a starting position.
Figure 8:
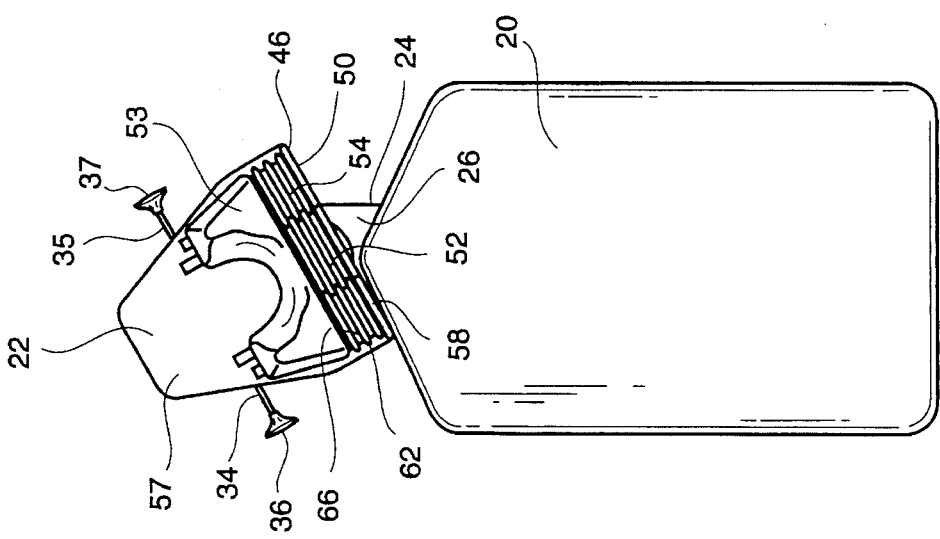
FIG. 8 is a top view of the cervical traction/stretch device shown in FIG. 1 and shows the platform of the device rotated 30 degrees to the right from the first position.

As shown in FIGS. 6, 7 and 8, the platform 22 can be rotated about a Y-axis which is perpendicular to the drawing sheet. In FIG. 6, the platform 22 is shown rotated about the Y-axis, approximately 30 degrees to the left of the starting position shown in FIG. 7.

In FIG. 8, the platform 22 is shown rotated about the Y-axis approximately 30 degrees to the right of the starting position shown in FIG. 7.

As shown in FIGS. 9, 10 and 11, the platform 22 can also be rotated about a Z-axis which is perpendicular to the drawing sheet as shown. The platform 22 can be rotated or tilted about the Z-axis 45 degrees upwardly, as shown in FIG. 9 from a starting position, shown in FIG. 10, where the platform 22 extends generally parallel to the inclined surface 14.

As shown in FIG. 11, the table or platform 22 also can be rotated approximately 30 degrees below the starting position as shown in FIG. 10. Also, a gauge 86 (shown in FIG. 10 only) can be provided for determining the amount of rotation of the platform 22 about the Z-axis.

Note that the platform 22 can be rotated in any combination of any of the three directions, at the same time. This allows a person to obtain isolated traction in a desired area.

In the use of the pivotable cervical traction/stretch and neck curve support device 10 of the present invention, a clinician will place the base portion 14 of the traction/stretch and neck curve support device 12 on a flat surface such as a floor and lay down on the inclined surface 16 or on the pad 20 on the inclined surface 16. The cervical curve of the patients neck must be received over the center of the U-shaped opening in both the bellows 54 and in the head portion 53. Then, a doctor or other medical technician will place the strap 70 over the head of the patient and secure it firmly to the fastening structure 68.

Next, the doctor or medical technician will adjust the position of the platform 22 about any one or all of the X, Y or Z axes in order to isolate traction in the desired area. If the desired settings are not known, various positions can be tried until a stretch occurs in the desired area. Once a desired position is achieved, gauges 84, 86 on the platform 22 can be read and recorded to preserve a record of the desired amount of rotation in the three directions for future use.

Next, the doctor or medical technician will pump the hand-held bulb 80 to pump up the bellows portion 54 to create traction on the cervical area of the patients neck supported by the surface portions of the head portion 53 as described in copending application Ser. No. 08/120,602.

After treatment has been completed, the release or relief valve 78 is operated to deflate the bellows portion 54.

If desired an electrically operated air pump (not shown) can be connected to the tubing 76 in place of the bulb type hand-operated air pump 80. Such an electronic pump will include a timer for cycling the electrical pump through intermittent pump and relief cycles thereby to apply intermittent traction to the patient's neck for treating soft tissue or disk dysfunctions, not limited to arthritis, of a patient. Intermittent traction/stretch is preferred by healthcare professionals as a method of treatment. In this modification, air can be pumped into or released from the bellows portion 54 under the control of a timer having several different time cycles.

A user, patient or clinician can achieve some of the same benefits of electrically controlled intermittent traction/ stretch by intermittently pumping the inflation bulb 80 and operating the release valve 78.

From the foregoing description, it will be apparent that the cervical traction/stretch and neck curve support device 12 of the present invention has a number of advantages, some of which have been described above and others of which are inherent in the invention.

Also from the foregoing description it will be apparent that modifications can be made to the pivotable cervical traction/stretch and neck curve support device 12 of the present invention without departing from the teachings of the invention.

Accordingly the scope of the invention is only to be limited as necessitated by the accompanying claims.

I claim:

1. A pivotable cervical traction/stretch and neck curve support device comprising:

a base portion having an upper end, an upper inclined surface extending upwardly to said upper end for supporting a person's upper body or torso and a lower surface for resting on a planar support surface;

a table or platform situated adjacent said upper end of said base portion and having an upper surface and a bottom surface;

mounting means attached to said upper end of said base and to said bottom of said platform for pivotally and rotatably mounting said platform to said upper end of said base and above said upper end of said base in a manner allowing rotation of said platform about any one of or all of an X-axis, a Y-axis and a Z-axis, said mounting means including means for securing the platform in a desired position;

a head portion having an inner end surface, a bottom surface and a head receiving surface including a shoulder with an adjacent occipital cervical pressure or lift surface for engaging a user's head, said bottom surface being slidably supported on said platform; and moving means positioned on said platform, including a bellows portion and operable by the user or a healthcare practitioner for incrementally moving said head portion on said platform outwardly from said inclined surface.

2. The pivotable cervical traction/stretch and neck curve support device of claim 1 wherein said platform has abutment means and said bellows portion is situated between said head portion and said abutment means.

3. The pivotable cervical traction/stretch and neck curve support device of claim 2 wherein said bellows portion has means for releasably attaching said bellows portion to said abutment means.

4. The pivotable cervical traction/stretch and neck curve support device of claim 2 wherein said head portion has means for releasably attaching said head portion to said bellows portion.

5. The pivotable traction/stretch and neck curve support device of claim 3 wherein said means for releasably attaching said bellows portion to said abutment means includes a loop and hook type fastening means.

6. The pivotable traction/stretch and neck curve support device of claim 4 wherein said means for releasably attaching said head portion to said bellows portion includes a loop and hook type fastening means.

7. The pivotable cervical traction/stretch and neck curve support device of claim 1 wherein said mounting means includes:

a mounting plate mounted on said base portion;

a post having one end mounted on said mounting plate and an outer end;

a ball mounted at said outer end of said post;

a bracket having a socket therein, said socket being received on said ball and said bracket being mounted to said platform, said ball being received in said socket and being rotatable about an X-axis, a Y-axis or a Z-axis.

8. The pivotable cervical traction/stretch and neck curve support device of claim 7 wherein said said securing means includes locking means for locking said platform or table at a desired position.

9. The pivotable cervical traction/stretch and neck curve support device of claim 8 wherein said locking means includes at least one control rod, said control rod being fully threaded through said mounting plate and engaging said ball when said platform is locked in position; and said control rod being partially unthreaded through said mounting plate and not engaging said ball when said platform is not locked in position.

10. The pivotable cervical traction/stretch and neck curve support device of claim 1 further including gauge means attached to said pivotable mounting means for indicating the amount of rotation of said platform about at least one of an X-axis, a Y-axis and a Z-axis.

11. The pivotable cervical traction/stretch and neck curve support device of claim 2 further including means, connected to said bellows, for pumping air into said bellows and for relieving or releasing air from said bellows.

12. The pivotable cervical traction/stretch and neck curve support device of claim 11 wherein said means for pumping air into or releasing air from said bellows includes means enabling air to be intermittently pumped into and released from said bellows for treating soft tissue or disk dysfunctions, not limited to arthritis, of a patient.

13. The pivotable cervical traction/stretch and neck curve support device of claim 11 wherein said means for pumping air into and for relieving air from said bellows includes a conduit and a bulb type air pump at the outer end of said conduit; said bulb type air pump having a one way inlet valve at an outer end thereof and, at an inner end thereof, a manually operated relief valve.

14. The pivotable cervical traction/stretch and neck curve support device of claim 11 wherein said means for pumping air into or relieving air from said bellows includes an electrically operated pump and a timer for controlling operation of said electrically operated pump whereby air can be intermittently pumped into and out of said bellows for treating soft tissue or disk dysfunctions, not limited to arthritis, of a patient.

15. The pivotable cervical traction/stretch and neck curve support device of claim 1 further including a head strap, fastening means on each side of said head portion and attachment means on one side of said strap adjacent at least each end of said strap for coupling with said fastening means on each side of said head portion.

16. The pivotable cervical traction/stretch and neck curve support device of claim 15 wherein said fastening means on each side of said head portion includes a loop and hook type fastening structure.

17. The pivotable cervical traction/stretch and neck curve support device of claim 1 wherein said head portion is made of a foam material.

* * * * *